(12) United States Patent
Dasgupta et al.

(10) Patent No.: US 7,183,095 B2
(45) Date of Patent: Feb. 27, 2007

(54) CELL CULTURE SYSTEM FOR SYNTHESIS OF INFECTIOUS HEPATITIS C VIRUS

(75) Inventors: Asim Dasgupta, Los Angeles, CA (US); Prasad S. Koka, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 587 days.

(21) Appl. No.: 10/096,039

(22) Filed: Mar. 11, 2002

(65) Prior Publication Data

US 2002/0197277 A1 Dec. 26, 2002

Related U.S. Application Data

(60) Provisional application No. 60/274,709, filed on Mar. 9, 2001.

(51) Int. Cl.
*C12N 5/00* (2006.01)
(52) U.S. Cl. .................. 435/235.1; 435/347; 435/373; 435/455; 435/69.7
(58) Field of Classification Search ............. 435/235.1, 435/347, 373, 455, 69.7
See application file for complete search history.

(56) References Cited

U.S. PATENT DOCUMENTS

| 5,621,007 | A | * | 4/1997 | Gribkoff et al. | ............. | 514/387 |
| 6,156,538 | A | * | 12/2000 | Andrews et al. | ............ | 435/69.1 |
| 6,277,380 | B1 | * | 8/2001 | Ueda et al. | ............... | 424/212.1 |
| 6,497,873 | B1 | * | 12/2002 | Whitt et al. | ................ | 424/93.2 |
| 6,569,422 | B1 | * | 5/2003 | van Loon et al. | .......... | 424/93.2 |
| 6,602,705 | B1 | * | 8/2003 | Barnett et al. | ............ | 435/320.1 |

FOREIGN PATENT DOCUMENTS

| WO | WO 99/04008 | 1/1999 |
| WO | 99/67362 | 12/1999 |

OTHER PUBLICATIONS

Benton, et al., "Signal-Mediated Import of Bacteriophage T7 RNA Polymerase Into the *Saccharomyces cerevisiae* Nucleus and Specific Transcription of Target Genes," *Mol. and Cell. Biol*, 10(1):353-360 (1990).
Blight, et al., "Efficient Initiation of HCV RNA Replication in Cell Culture," *Science*, 290:1972-73 (2000).
Bukh, et al., "Genetic Heterogeneity of Hepatitis C Virus: Quasispecies and Genotypes," *Seminars in Liver Dis.*, 15(1):41-63 (1995).
Chung, et al., "Hepatitis C Virus Replication is Directly Inhibited by IFN-α in a Full-Length Binary Expression System," *PNAS*, 98(17):9847-9852 (2001).
Das, et al., "A Small Yeast RNA Blocks Hepatitis C Virus Internal Ribosome Entry Site (HCV IRES)-Mediated Translation and Inhibits Replication of a Chimeric Poliovirus Under Translational Control of the HCV IRES Element," *J. Virol.*, 72(7):5638-5646 (1998).
Grakoui, et al., "Expression and Identification of Hepatitis C Virus Polyprotein Cleavage Products," *J. of Virol.*, 67(3):1385-1395 (1993).
Hagedorn, C.H., "The Hepatitis C Viruses," Springer-Verlag, Berlin, 1999 (Table of Contents).
Koka, et al., "Human Immunodeficiency Virus Type 1-Induced Hematopoietic Inhibition is Independent of Productive Infection of Progenitor Cells In Vivo," *J. Virol.*, 73(11):9089-9097 (1999).
Kolykhalov, et al., "Transmission of Hepatitis C by Intrahepatic Inoculation with Transcribed RNA," *Science*, 277:570-574 (1997).
Korner, et al., "Replication of Subgenomic Hepatitis C Virus RNAs in a Hepatoma Cell Line," *Science*, 285:110-113 (1999).
Lai and Ware, "Hepatitis C Virus Core Protein: Possible Roles in Viral Pathogenisis," *Curr. Topics in Micro and Imm.*, 242:117-134 (2000).
Moradpour, et al., "Continuous Human Cell Lines Inducibly Expressing Hepatitis C Virus Structural and Nonstructural Proteins," *Heptology*, 28(1):192-201 (1998).
Myung, et al., "Inducible Model to Study Negative Strand RNA Synthesis and Assembly of Hepatitis C Virus From a Full-Length cDNA Clone," *J. of Virol. Meth.*, 94:55-67 (2001).
Rice, C., "*Flaviviridae*: The Viruses and Their Replication," *Fields Virology*, Lippincott-Raven, Philadelphia, 931-959 (1996).
Yanagi, et al., "*In Vivo* Analysis of the 3' Untranslated Region of the Hepatitis C Virus After In Vitro Mutagenesis of an Infectious cDNA Clone," *PNAS*, 96:2291-2295 (1999).
Yanagi, et al., "Transcripts From a Single Full-Length cDNA Clone of Hepatitis C Virus are Infectious When Directly Transfected Into the Liver of a Chimpanzee," *PNAS*, 94:8738-8743 (1997).
Seipp, Stefanie et al., "Establishment of persistent hepatitis C virus infection and replication *in vitro*", *Journal of General Virology*, vol. 78, No. 10, pp. 2467-2476, 1997.
Yoo, Byoung J. et al., "Transfection of a Differentiated Human Hepatoma Cell Line (Huh7) with In Vitro-Transcribed Hepatitis C Virus (HCV) RNA and Establishment of a Long-Term Culture Persistently Infected with HCV", *Journal of Virology*, vol. 69, No. 1, pp. 32-38, 1995.

\* cited by examiner

*Primary Examiner*—Leon B Lankford, Jr.
(74) *Attorney, Agent, or Firm*—DLA Piper US LLP

(57) ABSTRACT

The invention rates to a hepatitis C virus (HCV) cDNA-based culture system capable of synthesis of infectious HCV in cell culture and cell-to-cell spread of the virus. The invention also relates to a method of measuring the level of HCV infection in a hepatocyte cell. A method for identifying a modulator of HCV activity is also presented, and a method for modulating HCV activity. The invention provides a reliable system for both genetic analysis of the viral genome and for the development of novel antiviral strategies.

32 Claims, 3 Drawing Sheets

CELL CULTURE SYSTEM FOR SYNTHESIS OF INFECTIOUS HEPATITIS C VIRUS

RELATED APPLICATIONS

This application claims priority under 35 U.S.C. §119(e) to U.S. Provisional Application No. 60/274,709 filed Mar. 9, 2001, herein incorporated by reference in its entirety.

FIELD OF THE INVENTION

The present invention relates generally to the field of virology and more specifically to the to the generation of hepatitis C virus (HCV) in a tissue culture system.

BACKGROUND OF THE INVENTION

Hepatitis C virus (HCV) establishes a chronic infection in a high percentage of infected individuals and is associated with progressive liver pathology, including cirrhosis and hepatocellular carcinoma. Antiviral drugs such as interferon alpha and ribavarin have had limited success in controlling HCV infection. As a result, it has become the leading cause for liver transplantation in the US. HCV is an enveloped virus containing a single stranded plus polarity RNA genome (~9500 nt) which is infectious when injected directly into livers of chimpanzees. The 5' untranslated region of viral RNA contains an internal ribosome entry site (IRES) which is used for translation of the single open reading frame into a large polyprotein. Viral structural and non-structural proteins are produced by proteolytic processing of the precursor. HCV has been a difficult virus to study due to the lack of an appropriate and reliable tissue culture system. The recent establishment of the HCV replicons that lack viral structural proteins has been a major advancement as it allows examination of viral gene expression and replication in tissue culture cells. However, the replicon based systems do not produce infectious virus as viral structural proteins are absent; consequently cell-to-cell spread of virus does not occur. Additionally, genetic analysis of the viral genome is hampered by the necessity of generating stable cell lines for the study of individual mutations.

The HCV polyprotein comprises, from the amino terminus to the carboxy terminus, the core protein (C), the envelope proteins (E1 and E2), and the non-structural proteins (NS2, NS3, NS4A, NS4B, NS5A and NS5B). C codes for the core nucleocapsid protein, E1 and E2 are envelope proteins that coat the virus, NS2, NS3 and NS4A are involved in proteolytic processing of the HCV polyprotein, NS5B has RNA polymerase and RNA helicase activity. The functions of NS4A and NS5B are unknown.

Though the RNA genome of HCV has recently been cloned, there remains a need for a reliable tissue culture system for the generation of HCV. Using conventional methods, RNA viruses such as poliovirus, are produced in cells by transfecting cells using RNA. Transfecting cells using viral cDNA from RNA viruses, such as poliovirus has not been successful in producing such viruses. It was expected that HCV, an RNA virus, would also readily be produced by a transfecting process using RNA, however such a method was found not to be suitable for HCV. Further, it was expected that transfecting cells using viral cDNA would not be a successful method of producing HCV. However, the present invention presents a method of synthesizing infectious HCV by transfecting hepatocyte cells with a gene encoding HCV and then exposing uninfected cells to the HCV to form additional HCV. This synthesis method has been found to be successful.

SUMMARY OF THE INVENTION

The present invention is based on the seminal discovery of a method for generation of infectious hepatitis C virus (HCV) in a tissue culture system. A transient, hepatitis C virus (HCV) cDNA-based expression system capable of synthesis of infectious HCV in cell culture is described herein. The system supports cell-to-cell spread of the virus. The validity of the system is demonstrated in the Examples by genetic analyses of replication-defective and replication-competent mutants of HCV. This invention provides a reliable system not only for genetic analysis of the viral genome, but also for the development of novel antiviral strategies.

In one aspect, the invention is directed to a culture system for generation of HCV. A cell culture medium is prepared from a cell culture made by transfecting a hepatocyte cell with a nucleic acid sequence encoding HCV and a nucleic acid sequence encoding RNA polymerase under conditions suitable for transfecting the cell, wherein, following transfection, the cell culture medium contains HCV.

Another aspect of the invention is directed to a method of measuring the level of infectivity of a hepatocyte cell infected with HCV in the culture system, as described above by measuring the amount of HCV-specific protein expressed on the cell surface of a cell in the culture system.

Yet another aspect of the invention is directed to a method of identifying a modulator of HCV activity, such as attachment, penetration, encapsulation, release, replication, translation or protein processing. The modulator is identified by contacting a test compound with the culture system described above and detecting an increase or decrease in HCV activity, such as attachment, penetration, encapsulation, release, replication, translation or protein processing. An increase or decrease in HCV activity, as compared with a culture system not contacted with the test compound identifies the test compound as a modulator.

In a related aspect, the present invention also includes a method for modulating HCV activity, such as attachment, penetration, encapsulation, release, replication, translation or protein processing. The method is performed by contacting a sample containing HCV with a modulator of HCV activity, such as attachment, penetration, encapsulation, release, replication, translation or protein processing that is selected using the method of identification described above.

In another aspect, the present invention is directed to a modulator identified as described above.

In another aspect, the present invention includes a method of diagnosing, modulating or treating an HCV-infected tissue or virus-associated tissue fibrosis by administering a modulator as described above.

In another aspect, the invention is directed to a kit for assaying a modulator of HCV activity, such as attachment, penetration, encapsulation, release, replication, translation or protein processing comprising the cells described above. In another embodiment, the kit contains instructions for use.

In yet another aspect, the invention is directed to a pharmaceutical composition containing a modulator identified as set forth above and a pharmaceutically acceptable carrier.

DETAILED DESCRIPTION OF THE INVENTION

Figure 1:
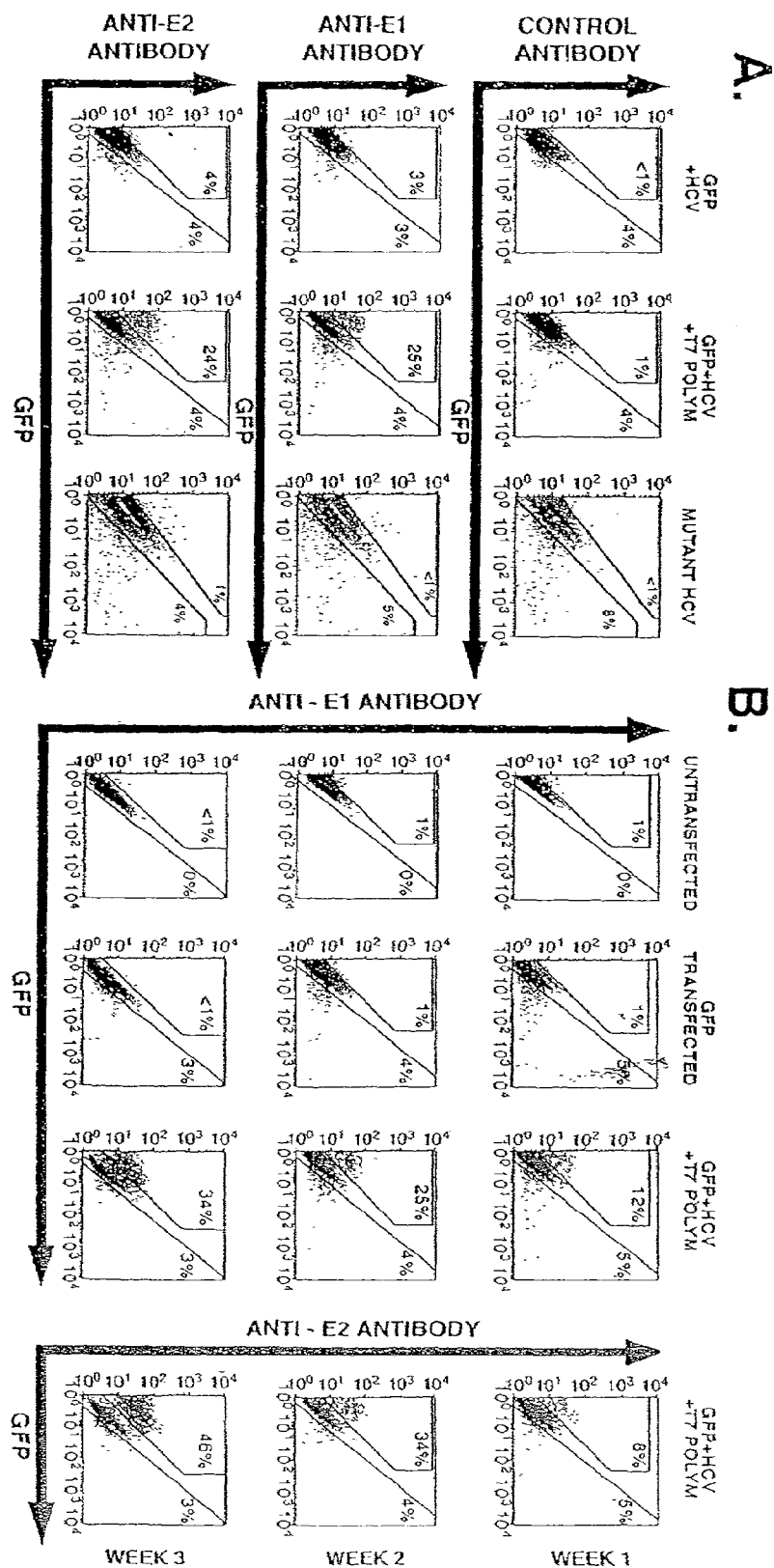
FIG. 1 Surface expression of HCV envelope proteins E1 and E2 by flow cytometry (FACS) E1/E2 surface expression was determined after cotransfection of 1×10⁷ Huh-7 cells with (A) pEGFP-N1 and pCVH77C (wt) (left panel), pEGFP-N1, pCVH77C and AR333126 (T7-plasmid) (middle panel), and pEGFP-N1, the stop codon mutant pSC1 and AR 3126 (right panel). FACS analyses of untransfected and pEGFP-N1 transfected cells are not shown as they are similar to those lacking AR3126. (B) Cell surface expression of E1 and E2 after 1, 2 and 3 weeks post transfection. The flow profiles of untransfected and pEGFP-N1 transfected cells labeled with anti-E2 antibody are similar to those for anti-E1 antibody and hence not shown.

The present invention relates to a tissue culture system for generation of Hepatitis C virus (HCV) and methods for use of the HCV so generated.

DEFINTIONS

The terms "Hepatitis C Virus" and "HCV" refer to the viral species that is the major etiological agent of BB-NANBH, the prototype isolate of which is identified in WO89/046699; EPO publication 318,216; and U.S. Pat. No. 5,350,671, the disclosures of which are incorporated herein by reference. "HCV" as used herein includes the pathogenic strains capable of causing hepatitis C, and attenuated strains or defective interfering particles derived therefrom. The HCV genome is comprised of RNA. It is known that RNA-containing viruses have relatively high rates of spontaneous mutation, reportedly on the order of $10^{-3}$ to $10^{-4}$ per incorporated nucleotide (Fields & Knipe, "Fundamental Virology" (1986, Raven Press, N.Y.)). As heterogeneity and fluidity of genotype are inherent characteristics of RNA viruses, there will be multiple strains/isolates, which may be virulent or avirulent, within the HCV species.

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin.

A "coding sequence of," a "nucleotide sequence encoding" or a "gene encoding" a particular polypeptide or protein, is a nucleic acid sequence which is transcribed and translated into a polypeptide or protein when placed under the control of appropriate regulatory sequences.

As used herein, a polynucleotide "derived from" a designated sequence refers to a polynucleotide sequence which is comprised of a sequence of approximately at least about 6 nucleotides, preferably at least about 8 nucleotides, more preferably at least about 10–12 nucleotides, and even more preferably at least about 15–20 nucleotides corresponding to a region of the designated nucleotide sequence. "Corresponding" means homologous to or complementary to the designated sequence. Preferably, the sequence of the region from which the polynucleotide is derived is homologous to or complementary to a sequence which is unique to an HCV genome. Whether or not a sequence is unique to the HCV genome can be determined by techniques known to those of skill in the art. For example, the sequence can be compared to sequences in databanks, e.g., Genebank, to determine whether it is present in the uninfected host or other organisms. The sequence can also be compared to the known sequences of other viral agents, including those which are known to induce hepatitis, e.g., HAV, HBV, and HDV, and to members of the Flaviviridae. The correspondence or non-correspondence of the derived sequence to other sequences can also be determined by hybridization under the appropriate stringency conditions. Hybridization techniques for determining the complementarity of nucleic acid sequences are known in the art. See also, for example, Maniatis et al. (1982). In addition, mismatches of duplex polynucleotides formed by hybridization can be determined by known techniques, including for example, digestion with a nuclease such as S1 that specifically digests single-stranded areas in duplex polynucleotides. Regions from which typical DNA sequences may be "derived" include but are not limited to, for example, regions encoding specific epitopes, as well as non-transcribed and/or non-translated regions.

The derived polynucleotide is not necessarily physically derived from the nucleotide sequence shown, but may be generated in any manner, including for example, chemical synthesis or DNA replication or reverse transcription or transcription. In addition, combinations of regions corresponding to that of the designated sequence may be modified in ways known in the art to be consistent with an intended use.

Similarly, a polypeptide or amino acid sequence "derived from" or "generated from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

A recombinant or derived polypeptide is not necessarily translated from a designated nucleic acid sequence or from an HCV genome; it may be generated in any manner, including for example, chemical synthesis, or expression of a recombinant expression system, or isolation from HCV, including mutated HCV. A recombinant or derived polypeptide may include one or more analogs of amino acids or unnatural amino acids in its sequence. Methods of inserting analogs of amino acids into a sequence are known in the art. It also may include one or more labels, which are known to those of skill in the art.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

"Amino acid" or "amino acid sequence" as used herein refer to an oligopeptide, peptide, polypeptide, or protein sequence, or to a fragment, portion, or subunit of any of these, and to naturally occurring or synthetic molecules.

The term "polypeptide", "peptide," "polyprotein" or "protein" as used herein, refers to amino acids joined to each other by peptide bonds or modified peptide bonds, i.e., peptide isosteres, and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphytidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Creighton, T. E., *Proteins—Structure and Molecular Properties 2nd Ed.,* W. H. Freeman and Company, New York (1993); *Posttranslational Covalent Modification of Proteins,* B. C. Johnson, Ed., Academic Press, New York, pp. 1–12 (1983)).

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "recombinant" means that the nucleic acid is adjacent to a "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the invention include nucleic acids such as expression vectors, self-replicating nucleic acids, viruses, integrating nucleic acids, and other vectors or nucleic acids used to maintain or manipulate a nucleic acid insert of interest. Typically, the enriched nucleic acids represent 15% or more of the number of nucleic acid inserts in the population of recombinant backbone molecules. More typically, the enriched nucleic acids represent 50% or more of the number of nucleic acid inserts in the population of recombinant backbone molecules. In a one embodiment, the enriched nucleic acids represent 90% or more of the number of nucleic acid inserts in the population of recombinant backbone molecules.

"Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., *J. Am. Chem. Soc.*, 85:2149–2154, 1963) (See also Stewart, J. M. and Young, J. D., *Solid Phase Peptide Synthesis, 2nd Ed.,* Pierce Chemical Co., Rockford, Ill., pp. 11–12)) and have recently been employed in commercially available laboratory peptide design and synthesis kits (Cambridge Research Biochemicals). Such commercially available laboratory kits have generally utilized the teachings of H. M. Geysen et al, *Proc. Natl. Acad. Sci., USA,* 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

A "promoter sequence," as used herein, is a site on DNA on the 5' end of a coding sequence, to which RNA polymerase will bind and initiate transcription. A promoter sequence is "operably linked to" a coding sequence when the RNA polymerase which initiates transcription at the promoter will transcribe the coding sequence into mRNA. It is envisioned that other regulatory elements, such as enhancers, may be useful in the invention as well.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

The term "purified viral polynucleotide" refers to an HCV genome or fragment thereof which is essentially free, i.e., contains less than about 50%, preferably less than about 70%, and even more preferably less than about 90% of polypeptides with which the viral polynucleotide is naturally associated. Techniques for purifying viral polynucleotides from viral particles are known in the art, and include for example, disruption of the particle with a chaotropic agent, differential extraction and separation of the polynucleotide(s) and polypeptides by ion-exchange chromatography, affinity chromatography, and sedimentation according to density.

The term "purified viral polypeptide" refers to an HCV polypeptide or fragment thereof which is essentially free, i.e., contains less than about 50%, preferably less than about 70%, and even more preferably less than about 90%, of cellular components with which the viral polypeptide is naturally associated. Techniques for purifying viral polypeptides are known in the art.

As used herein, the terms "culture," "cultured" or "culturing" refer to the growing of cells in vitro in a prepared medium. As used herein, a "culture system" is a cell culture including cells generating viral particles. In particular, a culture system of the invention includes cells in culture that generate HCV.

"Recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vector or other transfer DNA, and include the progeny of the original cell which has been transfected. It is understood that the progeny of a single parental cell may not necessarily be completely identical in morphology or in genomic or total DNA complement as the original parent, due to natural, accidental, or deliberate mutation.

A "replicon" is any genetic element, e.g., a plasmid, a chromosome, a virus, a cosmid, etc. that behaves as an autonomous unit of polynucleotide replication within a cell; i.e., capable of replication under its own control.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term "control sequences" is intended to include, at a minimum, all components whose presence is necessary for expression, and may also include additional components whose presence is advantageous, for example, leader sequences.

An "open reading frame" (ORF) is a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, and recombinant polynucleotide sequences.

"Immunologically identifiable with/as" refers to the presence of epitope(s) and polypeptides(s) which are also present in the designated polypeptide(s), usually HCV proteins. Immunological identity may be determined by antibody binding and/or competition in binding; these techniques are known to those of average skill in the art.

As used herein, "epitope" refers to an antigenic determinant of a polypeptide. An epitope could comprise 3 amino acids in a spatial conformation which is unique to the epitope. Generally an epitope consists of at least 5 such amino acids, and more usually, consists of at least 8–10 such amino acids. Methods of determining the spatial conformation of amino acids are known in the art, and include, for example, x-ray crystallography and 2-dimensional nuclear magnetic resonance.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is immunologically reactive with an antibody are known in the art.

As used herein, the term "transfection" refers to the uptake of foreign DNA by a cell in culture.

As used herein, the term "immunogenic polypeptide" is a polypeptide that elicits a cellular and/or humoral immune response, whether alone or linked to a carrier in the presence or absence of an adjuvant.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

"Treatment" as used herein refers to prophylaxis and/or therapy.

An "individual", as used herein, refers to vertebrates, particularly members of the mammalian species, and includes but is not limited to domestic animals, sports animals, and primates, including humans.

As used herein, the "sense strand" of a nucleic acid contains the sequence that has sequence homology to that of mRNA. The "anti-sense strand" contains a sequence which is complementary to that of the "sense strand".

As used herein, a "positive stranded genome" of a virus is one in which the genome, whether RNA or DNA, is single-stranded and which encodes a viral polypeptide(s). Examples of positive stranded RNA viruses include Togaviridae, Coronaviridae, Retroviridae, Picornaviridae, and Caliciviridae. Included also, are the Flaviviridae, which were formerly classified as Togaviradae. See Fields & Knipe (1986).

As used herein, "purified HCV" refers to a preparation of HCV which has been isolated from the cellular constituents with which the virus is normally associated, and from other types of viruses which may be present in the infected tissue. The techniques for isolating viruses are known to those of skill in the art, and include, for example, centrifugation and affinity chromatography.

The term "HCV particles" as used herein include entire virion as well as particles which are intermediates in virion formation. HCV particles generally have one or more HCV proteins associated with the HCV nucleic acid.

As used herein, the term "probe" refers to a polynucleotide which forms a hybrid structure with a sequence in a target region, due to complementarity of at least one sequence in the probe with a sequence in the target region.

As used herein, the term "target region" refers to a region of the nucleic acid which is to be amplified and/or detected.

As used herein, the term "viral RNA", which includes HCV RNA, refers to RNA from the viral genome, fragments thereof, transcripts thereof, and mutant sequences derived therefrom.

As used herein, a "biological sample" refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

As used herein, a "plasmid" is a self-replicating, circular, double-stranded DNA molecule. Often, a plasmid is cleaved with a restriction enzyme, foreign DNA is inserted and the plasmid is transferred into a cell. "Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion, gel electrophoresis may be performed to isolate the desired fragment.

"Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

The phrase "substantially identical" in the context of two nucleic acids or polypeptides, refers to two or more sequences that have at least 60%, 70%, 80%, and in some aspects 90–95% nucleotide or amino acid residue identity, when compared and aligned for maximum correspondence, as measured using one of the known sequence comparison algorithms or by visual inspection. Typically, the substantial identity exists over a region of at least about 100 residues, and most commonly the sequences are substantially identical over at least about 150–200 residues. In some embodiments, the sequences are substantially identical over the entire length of the coding regions.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucin, valine, leucine, or methionine, for another, or substitution of one polar amino acid for another, such as substitution of arginine for lysine, glutamic acid for aspartic acid or glutamine for asparagine).

"Fragments" as used herein are a portion of a naturally occurring protein which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related. In general two amino acid sequences are "substantially the same" or "substantially homologous" if they are at least about 85% identical. Fragments which have different three dimensional structures as the naturally occurring protein are also included. An example of this, is a "pro-form" molecule, such as a low activity proprotein that can be modified by cleavage to produce a mature enzyme with significantly higher activity.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5X SSPE, 0.3% SDS, and 200 n/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "variant" refers to polynucleotides or polypeptides of the invention modified at one or more base pairs, codons, introns, exons, or amino acid residues (respectively) yet still retain the biological activity of NS3. Variants can be produced by any number of means included methods such as, for example, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, and any combination thereof.

DESCRIPTION

A transient, hepatitis C virus (HCV) cDNA-based expression system capable of synthesis of infectious HCV in cell culture is described. The system supports cell-to-cell spread of the virus. The validity of the system is demonstrated in the Examples by genetic analyses of replication-defective and replication-competent mutants of HCV. Virus isolated from the culture media after three serial passages of the transfection-derived supernatants infects naive Huh-7 cells and synthesizes virus-coded proteins and viral plus and minus-strand RNA. Immunogold electron microscopy reveals intracellular (cytoplasmic) synthesis of 40–60 nm size HCV particles and significant cellular damage. This study provides a reliable system not only for genetic analysis of the viral genome, but also for the development of novel antiviral strategies.

In one aspect, the invention is directed to a culture system for generation of HCV. A cell culture medium is prepared from a cell culture. The cell culture is prepared by transfecting a hepatocyte cell with a nucleic acid encoding HCV and a nucleic acid sequence encoding RNA polymerase under conditions suitable for transfecting the cell, wherein, following transfection, the cell culture medium contains HCV. In one embodiment, the cell culture medium is further exposed to a non-transfected hepatocyte cell, wherein HCV is secreted from the non-transfected hepatocyte cell. This step may be repeated multiple times in order to obtain multiple cells infected with HCV. In another embodiment, the non-transfected hepatocyte cell is co-cultured with the transfected cell. In yet another embodiment, the culture system further comprises isolation of the cell culture medium. In yet another embodiment, the culture system further comprises transfecting the cell with a nucleic acid sequence encoding NS3 and NS5B. In one embodiment, the hepatocyte cell is a hepatocellular carcinoma cell, and in another embodiment, a human hepatocellular carcinoma cell, such as Huh-7. The level of expression of HCV in the hepatocellular carcinoma cells such as Huh-7 is greater than other cells such as human uterine cervical carcinoma cell line (HeLa) as shown in Table 1. The hepatocellular carcinoma cells may also be, for example, HepG2, C3A or PLC. The cells may also be B cells. The transfected and nontransfected cells of the invention may be two different cell types. There are at least 6 HVC genotypes and more than 50 subtypes. The types of HCV used in the present invention may include, but are not limited to: 1a, 1b, 1c, 2a, 2b, 2c, 2i, 3a, 3b, 3c, 4a, 4b, 4c, 4d, 4e, 4f, 4g, 4h, 5a, and 6a. In one embodiment the HCV is type 1a HCV. In a further aspect, the invention is directed to HCV produced by this method as well as the cotransfected cells.

In another embodiment, the cell culture is produced by transfecting the nucleic acid encoding HCV and the nucleic acid encoding the RNA polymerase into a single plasmid. In a preferred embodiment, the nucleic acid encoding HCV and the nucleic acid encoding the RNA polymerase are transfected into two separate plasmids. Where the culture system further comprises transfecting the cell with a nucleic acid sequence encoding NS3 and NS5B, the nucleic acid encoding HCV and the nucleic acid encoding the RNA polymerase and the nucleic acid sequence encoding NS3 and NS5B may be transfected into a single plasmid, or multiple plasmids, up to three separate plasmids.

Any promoter on the HCV DNA plasmid that corresponds to the RNA polymerase gene can be used in the methods of the invention. In one embodiment, the promoter is a T7 promoter and the RNA polymerase is a T7 RNA polymerase under the control of a CMV promoter. Any suitable nucleic acid that regulates transcription can be used as a promoter such as the $P_L$, tac, trp, trc, T3, T7, β-galactosidase, lacZ, SP6, SV40, QB or CMV promoter in conjunction with any corresponding RNA polymerase gene that encodes RNA polymerase. Therefore, polymerases of the invention may include, but are not limited to polymerases associated with the promoters $P_L$, tac, trp, trc, T3, T7, β-galactosidase, lacZ, SP6, SV40, QB and CMV. In one embodiment the promoter is SP6 and the RNA polymerase is a SP6 RNA polymerase. In another embodiment, the promoter is QB and the RNA polymerase is a QB RNA polymerase.

The T7 RNA polymerase of the invention is present in the cytoplasm and will transcribe the HCV cDNA following the T7 promoter, to generate HCV RNA. The viral RNA is then translated to produce viral structural (core, E1, E2 and p7) and nonstructural (NS2, NS3, NS4A, NS4B, NS5A and NS5B) proteins. Viral RNA replication directed by the RNA-dependent RNA polymerase (NS5B) would then occur. Where progeny virons are made and secreted into the culture medium, these viral particles may infect additional cells, resulting in spread of the virus. Methods of monitoring the viral protein synthesis are exemplified in the Examples, and include, but are not limited to, fluorescent activated cell sorting (FACS) and immuno gold electron microscopy.

FACS analyses early after transfection is likely to detect E1/E2 surface expression on cells initially transfected by HCV plasmids. However, infection of neighboring cells with newly made virus released from transfected cells should also lead to E1/E2 surface expression on those neighboring cells. Thus, the number of E1/E2 positive cells should increase with time following transfection.

A visualization of in vitro synthesized HCV 1a type particles by immuno gold electron microscopy using Huh-7 cells infected with a 4th passaged virus preparation and staining the cells with human anti E1 and anti E2 antibodies (intracellular staining) and a second antibody (anti-human IgG) linked to 10 nm gold particles indicated that virus particles were synthesized in infected cells.

Detection of HCV plus and minus strand RNA in supernatants (media) recovered from cells transfected with HCV has been performed by RT-PCR. Comparisons have been made among cells transfected with GFP; GFP and HCV; GFP, HCV and T7 Polymerase (upper panel). HCV minus strand synthesis can be seen in infections by supernatants recovered from HCV plus T7 polymerase transfected cells. Detection of minus strand indicates replication of viral RNA. Results of quantitative RT-PCR for HCV plus and minus strand RNA synthesis showed that 400 copies of plus strand and 45 copies of minus strands per cell are synthesized in virus infected cells.

Another aspect of the invention is directed to a method of measuring the level of infectivity of a hepatocyte cell infected with HCV in the culture system, as described above by measuring the amount of HCV-specific protein expressed on the cell surface of a cell in the culture system. HCV consists of the following proteins: C, E1, E2, NS2, NS3, NS4A, NS4B, NS5A and NS5B. The HCV-specific proteins expressed on the cell surface of a cell in the culture system may be E1, E2, NS5A or NS3 proteins.

Another aspect of the invention is directed to a method of identifying a modulator of HCV activity, such as attachment, penetration, encapsulation, release, replication, translation or protein processing. The modulator is identified by contacting a test compound with the culture system described above and detecting an increase or decrease in HCV activity, such as attachment, penetration, encapsulation, release, replication, translation or protein processing. An increase or decrease in HCV activity, as compared with a culture system not contacted with the test compound identifies the test compound as a modulator. If a decrease is detected, the modulator is an inhibitor of HCV attachment, penetration, encapsulation, release, replication, translation or protein processing. If an increase is detected, then the modulator is an activator of HCV attachment, penetration, encapsulation, release, replication, translation or protein processing. In one embodiment, such activities are measured by measuring expressed HCV-specific proteins on the cell surface of a cell in the culture system, infected with HCV. Such proteins may include E1, E2, NS5A or NS2 proteins. In one embodiment, the modulator is a protein. In another embodiment, the modulator is a nucleic acid molecule. In yet another embodiment, the modulator is a peptide, peptidomimetic, or other small molecule.

In a related aspect, the present invention also includes a method for modulating HCV activity, such as attachment, penetration, encapsulation, release, replication, translation or protein processing. The method is performed by contacting a sample containing HCV with a modulator of HCV activity, such as attachment, penetration, encapsulation, release, replication, translation or protein processing that is selected using the method of identification described above. In one embodiment, the modulator is a protein. In another embodiment, the modulator is a nucleic acid molecule. In yet another embodiment, the modulator is a peptide, peptidomimetic, or other small molecule. Such a sample comprises any fluid containing HCV.

In yet another aspect, the invention is directed to a pharmaceutical composition containing a modulator identified as set forth above and a pharmaceutically acceptable carrier. In one embodiment, the modulator is a protein. In another embodiment, the modulator is a nucleic acid molecule. In yet another embodiment, the modulator is a peptide, peptidomimetic, or other small molecule.

Additionally, the present invention includes a method of diagnosing, modulating or treating an HCV-infected tissue or virus-associated tissue fibrosis by administering a modulator as described above. In one embodiment, the modulator is a protein. In another embodiment, the modulator is a nucleic acid molecule. In yet another embodiment, the modulator is a peptide, peptidomimetic, or other small molecule.

In another aspect, the invention is directed to a kit for assaying a modulator of HCV activity, such as attachment, penetration, encapsulation, release, replication, translation or protein processing comprising the cells described above. In a preferred embodiment, the kit contains instructions for performing the assay, which instructions may be printed on a package insert, packaging or label included in the kit. The printed matter can also be included on receptacles included in the kit, and indicia of sample and reagent volumes can be indicated in the test receptacle. The precise instructions would vary depending upon the substance to be detected and/or detection method used, but may include instructions for one or more of the following: instructions for dilution of the kit components and/or preparation of the sample, directions for volume or concentration of substance used for each assay, volume of sample to add to the assay, directions for labeling the reactants, directions for taking measurements of components, preferred temperature conditions, and timing of component addition and mixing, and use of a standard to calibrate test results.

The following examples are intended to illustrate but not limit the invention.

EXAMPLES

Example 1

Synthesis of Infectious Hepatitis C Virus In vitro in a Tissue Culture System

A reliable cDNA-based tissue culture assay for the synthesis of infectious hepatitis C virus (HCV) has been developed.

Transfection of cloned, wt HCV(1a) cDNA into human hepatocellular carcinoma (Huh-7) cells under specific conditions resulted in cell surface expression of viral glycoproteins E1 and E2. Both viral structural and non-structural NS5A and NS3) protein expression increased up to three weeks of transfection. Supernatants (media) isolated from the cell culture were infectious when mixed with fresh Huh-7 cells. The infectivity of the culture supernatants was resistant to treatments by DNase and a RNase. The virus titer increased significantly after four passages and cells infected with the passaged virus showed synthesis of both viral proteins and viral positive and negative strand RNA. No infectious virus could be recovered from Huh-7 cells transfected with a mutant HCV cDNA clone. Two inhibitors that block HCV-IRES-mediated translation efficiently, inhibited synthesis of infectious virus. Both density gradient centrifugation and initial electron microscopy showed that intact virus particles were being made in this system.

Example 2

Replication of Hepatitis C Virus in Huh-7 Cells

Cell Culture

Human hepatocellular carcinoma Huh-7 cells were cultured in 1640 RPMI containing 10% fetal bovine serum, penicillin, streptomycin, and L-glutamine.

Plasmid DNA Reagents

The cDNA clone of hepatitis C virus (HCV), pCV-H77C, was kindly provided by Drs. Jens Bukh and Robert Purcell of NIH, Bethesda, Md. Transcription of HCV genome in this construct is directed by the bacteriophage T7 promoter. Plasmid DNAs, AR3126 and AR3132, containing the T7 RNA dependent RNA polymerase gene and eucaryotic transcription initiation and termination signals, were kindly provided Dr. F. William Studier, Brookhaven National Laboratory, Upton, N.Y. EGFP-N1 plasmid DNA encoding the renilla reniformis green fluorescence protein was purchased from Promega Biotec, Madison, Wis.

Transfection of Huh-7 Cells

Transfections were performed with appropriate plasmid DNAs using Superfect reagent from BIGCO.BRL Life Technologies. $10 \times 10^6$ cells contained in a T-75 tissue culture flask were treated with Superfect containing 15 micrograms of each plasmid DNA.

Harvesting of Virus from Supernatants and Treatment of Huh-7 Cells

Supernatants were harvested from transfected cells at regular time periods and stored at −70C. These harvested supernatants were used to treat Huh-7 cells for infection with HCV particles contained in the supernatants.

Flow Cytometry for HCV Envelope Expression

Transfected or supernatant treated Huh-7 cells were stained with anti-E1 or anti-E2 antibodies using procedures similar to those described previously by Koka et al. A goat anti-mouse IgG1 antibody conjugated to PE was used for labeling of the primary antibody. Flow cytometric analyses were performed on a Becton-Dickinson FACSCAN.

RNA Isolation and RT-PCR of HCV RNA

RNA was isolated by the Qiagen kit according to protocols provided by the manufacturer. Isolated RNA was amplified by using 20-mer direct and reverse primers to generate a 530 bp DNA fragment at the 5'-end of HCV positive strand RNA, and a 480 bp fragment at the 3'-end of the viral negative strand.

Intracellular Flow Cytometry to Detect HCV Nonstructural Proteins

The one step cell permeabilization and antibody staining kit was purchased from BD-Pharmingen and used according to the protocols provided by the manufacturer.

Example 3

Transfection

To develop an HCV cDNA-based tissue culture system, an infectious HCV type 1a cDNA (pCV-H77C (M. Yanagi et al. Proc. Natl. Acad. Sci. USA 94, 8738 (1997).)) was co-transfected under the control of the T7 promoter with the T7 RNA polymerase gene under the SV-40 promoter (AR 3126 (B. M. Benton, W. K. Eng, J. J. Dunn, F. W. Studier, R. Sternglanz, P. A. Fisher. Molecular Cell Biol. 10, 353 (1990).). The latter construct lacked the nuclear localization signal.

Huh-7 cells ($1\times10^7$) were transfected/co-transfected with plasmid DNA at 60–70% confluency in T-75 tissue culture flasks. In some experiments transfection was carried out in 6-well plates ($3\times10^6$ cells per well and 2 μg of each plasmid). Ten μgs of each plasmid was added to 0.45 ml of serum-free RPMI and mixed with 180 μl of superfect transfection reagent from Quiagen. The mixture was incubated at room temperature for 10 min after which 3 ml of RPMI containing 10% fetal bovine serum was then added. The mixture was then layered on Huh-7 cells and incubated at 37° C. for 6 h. The cell culture medium was changed regularly until the cells were harvested for labeling with appropriate antibodies or RNA isolation.

Example 4

Viral Protein Synthesis

It was hypothesized that the T7 RNA polymerase made in the cytoplasm should transcribe the HCV cDNA under the T7 promoter to generate high quantities of HCV RNA. The viral RNA would then be translated to produce viral structural (core, E1, E2 and p7) and nonstructural (NS2, NS3, NS4A and B, NS5A and B) proteins. Presumably viral RNA replication directed by the RNA-dependent RNA polymerase (NS5B) would then occur. If progeny virions were made and secreted into the tissue culture media, these newly made virus particles could infect neighboring cells resulting in cell-to-cell spread of virus.

Viral protein synthesis was monitored by assaying cell surface expression of viral envelope proteins E1 and E2 by fluorescent activated cell sorting (FACS). Cell surface expression of HCV E1 and E2 was determined by flow cytometry following a procedure as previously described. (P. Koka, B. D. Jamieson, D. G. Brooks, J. A. Zack J. Virol. 73,9089 (1999). Anti-E1 and anti-E2 antibodies (Lot No. C569617) were purchased from Austral Biologicals, San Ramon, Calif. Isotype antibody (human IgG was used as control. Antibody titers ranged up to dilution of 1:400 to eliminate background staining of control cells. The mouse anti-E1/E2 antibodies labeled with phycoerythrin (PE) were used as secondary antibody for 30 min at 4° C. and cell pellets were washed with PBS by centrifugation at 3000 rpm for 3 min, prior to and after labeling with antibodies.

FACS analyses after transfection will detect both E1/E2 surface expression on cells initially transfected by pCVH77C and AR3126 plasmids and E1/E2 surface expression on infected neighboring cells by newly made virus released from transfected cells. Thus, the number of E1/E2 positive cells is expected to increase with time following transfection. Twenty-five percent of the Huh-7 cells became E1/E2 positive 10 days after cotransfection with the pCVH77C and AR3126 plasmids compared to 1% positive cells with a control antibody (FIG. 1A). Omission of the T7 plasmid from the transfection resulted in significant reduction of E1/E2 surface expression (3–4%). That E1/E2 expression was dependent on viral protein synthesis was confirmed by the inability of a mutant H77C plasmid, in which a stop codon was introduced into the ORF, to induce E1/E2 expression (FIG. 1A). Also cotransfection of cells with a plasmid encoding a known HCV IRES inhibitor (called IRNA or inhibitor RNA; S. Das, et al. J. Virol. 72:5638 (1998).) totally blocked E1/E2 surface expression. All transfection reactions contained a control plasmid encoding the green fluorescent protein (EGFP) to assess transfection efficiency. A time course of E1/E2 surface expression following cotransfection showed gradual increase in E1/E2 positive cells from 8–12% at week 1 to 25–34% at week 2, and finally to 34–46% at week 3 (FIG. 1B). The differences seen between E1 and E2 expression may be due to differential sensitivities of the antigen specific antibodies used in the assay. Both IFN-alpha and gamma, inhibited E1/E2 expression only marginally. This was expected because the type 1a virus is largely resistant to the effects of IFN.

Example 5

In vitro Protein Synthesis

To determine whether infectious progeny virions were being shed into the media, cell culture media were isolated from cells co-transfected with H77C and AR3126 plasmids followed by digestion with a mixture of DNase and RNase or with buffer alone. While the cells infected with the buffer-treated culture supernatant showed surface expression of E2 on 89% cells, 82% of the cells were E2 positive following infection with the DNase/RNase-treated supernatant. A control experiment showed total degradation of control DNA and RNA samples under the conditions used for nuclease digestion. These results showed that DNase and RNase resistant viral particles were being secreted from the transfected cells.

Viral replication in supernatant-infected cells was examined by reverse transcription-polymerase chain reaction (RT-PCR) using appropriate primers to detect viral positive and negative strand RNA. Prior to infection of Huh-7 cells with these supernatants, each supernatant (5 ml) with a viral titer of 1500–4000 copies/ml was treated with 1 μl of Danes-free pancreatic Raze (Roche) and 5 μl of RQ1 RNAse-free DNAse (Promega) for 15 min at 37° C., sufficient to completely digest 10 μg of DNA or RNA. For standards, in vitro transcribed positive and negative strand RNAs from the pCVH77C clone were generated by cutting the plasmid with Xbal or Ndel, respectively. RT-PCR analyses were performed using oligonucleotide primer pairs to detect the 5'-end of positive strand RNA of 560 base pairs (bp) and the 5'-end of the negative strand RNA to generate a 430 bp amplified product. The complementary primer 5'-CCTTAC-CCAAATTGCGCGAC-3' (SEQ ID NO:1) to the positive strand was used for the RT reaction. The samples were then treated with RNAse as above. The 560 bp product was amplified using 5'-AGC TAG GCC GAG AGC CAC GG-3' (SEQ ID NO:2) and 5'-TGT CGT GCA GCC TCC AGG AC-3' (SEQ ID NO:3) primer pair. The 430 bp product was amplified with the primary pair 5'-GCT TCT GTC CAG AGG AGG CA-3' (SEQ ID NO:4) and 5'-GTC ATG CGG CTC ACG GAC CT-3' (SEQ ID NO:5), following RT with the complementary pair 5'-AGAGAGGCCAGTATCAG-CAC-3' (SEQ ID NO:6) to the negative strand and RNAse digestion. The PCR amplifications were subjected to 40 cycles each for 1 min at 94° C. for denaturation, 60° C. for hybridization, and 72° C. for elongation. The β-actin RNA was used as internal control to generate a 285 bp amplified product using primer pairs purchased from Promega Corp., Madison, Wis. A 26-mer direct primer 5'-OH-TCA TGA AGT GTG ACG TTG ACA TCC GT-3' (SEQ ID NO:7) and a 26 mer reverse primer 5'-OH-CCT AGA AGC ATT TGC GGT GCA CGA TG-3' (SEQ ID NO:8) were utilized. This reaction is incubated for amplification as prescribed by the manufacturer as follows: 2 minutes at 94° C., 40 cycles of (94° C.-30 seconds for denaturation, 65° C.-1 minute for hybridization, and 68-2 minutes for elongation).

Cell culture media (5 ml, approximately 1500 copies per ml) recovered from cells transfected with pCVH77C and pEGFP-N1 or pCVH77C, pEGFP-N1 and AR3126 were treated with DNAse and RNAse as described in Example 5, then used to infect fresh Huh-7 cells. After 8 days, total cellular RNA was isolated and subjected to qualitative RT-PCR analyses to detect the 560 bp plus and 430 bp minus PCR products. In vitro transcribed positive and engative strand RNAs generated by transcription from linearalized pCVH77C were amplified using the same sets of primers. Only the 560 bp long HCV (+) strand PCR product was detected in cells infected with the supernatant recovered from pCVH77C transfected cells. However, both the 560 bp long plus and the 430 bp long minus strand PCR products were detected in cells infected with the culture media from pCVH77C and AR3126 co-transfected cells, a finding consistent with the production of the negative strand RNA found during RNA replication. No minus-strand PCR product was detected in the media harvested from pCVH77C and AR3126 co-transfected cells. These results show that supernatants recovered from cells transfected with pCVH77C and AR3126 plasmids contain virus particles capable of infecting naive Huh-7 cells in culture. These results also show that small amounts of viral particles are produced in cells transfected with the pCVH77C plasmid alone. However, when fresh cells are infected with this preparation, active replication as measured by negative strand RNA synthesis is not observed although the input plus strand RNA is detected.

Similar, if not identical, results were obtained when the plasmids were introduced into cells by electroporation rather than lipofection.

Example 6

Viral Replication in Mutant Constructs

Mutant constructs that were previously shown to be either non-infectious in chimpanzees (M. Yanagi et al. Proc. Natl. Acad. Sci. USA 96, 2291 (1999).) or defective in RNA replication in the replicon-based assay (V. Lohman et al. Science 285, 110 (1999); K. J. Blight, A. A. Kolykholv, C. M. Rice. Science 290, 1972 (2000).) were used in the present Example. The three (type 1a) 3' UTR X-region deletion mutants (−98X, X-52, −42X) were previously found to be non-infectious in chimpanzees while the variable region deletion mutant (V-24) was infectious and induced disease in chimpanzees (M. Yanagi et al. Proc. Natl. Acad. Sci. USA 96, 2291 (1999).). The NS5B mutant where the GDD motif is changed to AAG in the type 1b background has been shown to be completely defective in RNA replication in the replicon-based assay (V. Lohman et al. Science 285, 110 (1999); K. J. Blight, A. A. Kolykholv, C. M. Rice. Science 290, 1972 (2000).). All five mutant constructs showed similar levels of surface expression of E1 during initial transfection with the DNA constructs indicating viral proteins were synthesized following transcription by T7 RNA polymerase in transfected cells. The cell surface expression of HCV E1 following initial transfection by the wt and mutant plasmids were as follows: pCVH77C, (35%); GDD mutant (22%); −98x (29%); −42x (39%); X-52 (30%) and VR-24 (38%).

RT-PCR analyses of total RNA from cells infected with supernatants harvested from wt and mutant pCVH77C transfected cells. Huh-7 cells were transfected with wt pCVH77C, the NS5B GDD mutant (GDD→AAG), 3'-UTR X region deletion mutants −98X, −42X and X-52 and the variable region deletion mutant VR-24 (M. Yanagi et al. Proc. Natl. Acad. Sci. USA 96, 2291 (1999).). All transfection reactions included plasmid AR3126. Tissue culture media (5 ml) recovered from transfected cells was used to infect fresh Huh-7 cells for 8 days. Total RNA recovered from infected cells were analyzed by RT-PCR for the presence of 560 bp (+) and 430 bp (−) strand RNA as described above. Approximately 10 fold more RNA was used for detection of viral (−) strand than that used for (+) strand detection. When fresh cells were infected with the tissue culture media harvested from wt and mutant DNA-transfected cells, E1/E2 surface expression was detected on cells infected with the wt and VR-24 transfection-derived culture media. The −98X, X-52, −42X and the GDD mutants showed only background levels of E1/E2 expression. RT-PCR analyses of total cellular RNA showed synthesis of both viral (+) and (−) strand-specific PCR products from wt and VR-24 infected cells, while no plus and minus-strand RNA could be detected in cells infected with −98X, −42X, X-52 and the GDD mutants. No viral DNA contamination was apparent in these RNA preparations by PCR analysis. Also no evidence of integrated viral DNA in the total DNA isolated from infected cells was found.

Example 7

Elimination of Contamination

To rule out the possibility that the DNase/RNase treated culture supernatants might be contaminated with either viral cDNA or RNA, the culture supernatants containing the putative infectious HCV particles were serially passaged 3 times in Huh-7 cells. Only virus particles secreted into the medium were used to infect cells during each passage and the culture media recovered from the final passage with an approximate titer of 3–5×10$^4$ RNA copies/ml was used to infect Huh-7 cells for 0, 3, 7 and 10 days.

RT-PCR of total cellular RNA recovered from cells infected with passaged virus was performed. The DNAse/RNAse-treated tissue culture media recovered from the experiment shown in Example 5 was passaged 3 times in Huh-7 cells. Culture supernatant (5 ml) from the final passage with an approximate titer of 40,000 genome equivalents per ml was used to infect 1×10$^7$ Huh-7 cells. Total RNA isolated from Huh-7 cells infected with the passaged virus for 0, 3, 7, 10 and 20 days was used to monitor viral plus and minus strand RNA by RT-PCR. RNA isolated from approximately 10$^6$ and 10$^7$ cells were used for detection of (+) and (–) RNA, respectively. Both viral (+) and (–) strand RNA were detected after 3 days of infection and RNA synthesis gradually increased up to 20 days. The RT-PCR data was quantitated by generating linear standard curves using amplified DNA from known amounts of in vitro transcribed plus and minus strand RNA. For the quantitation of beta-actin, amplified DNA was generated by RT-PCR of RNA extracted from known number of cells as indicated. From these results, the number of molecules of plus and minus strand RNA per cell was estimated to be 350 and 25, respectively. Quantitative RT-PCR revealed that the ratio of (+) to (–) RNA per cell at a given time was approximately 15:1. Preliminary results indicate that actinomycin D-resistant viral RNA is synthesized in cells infected with the passaged virus.

Figure 2:
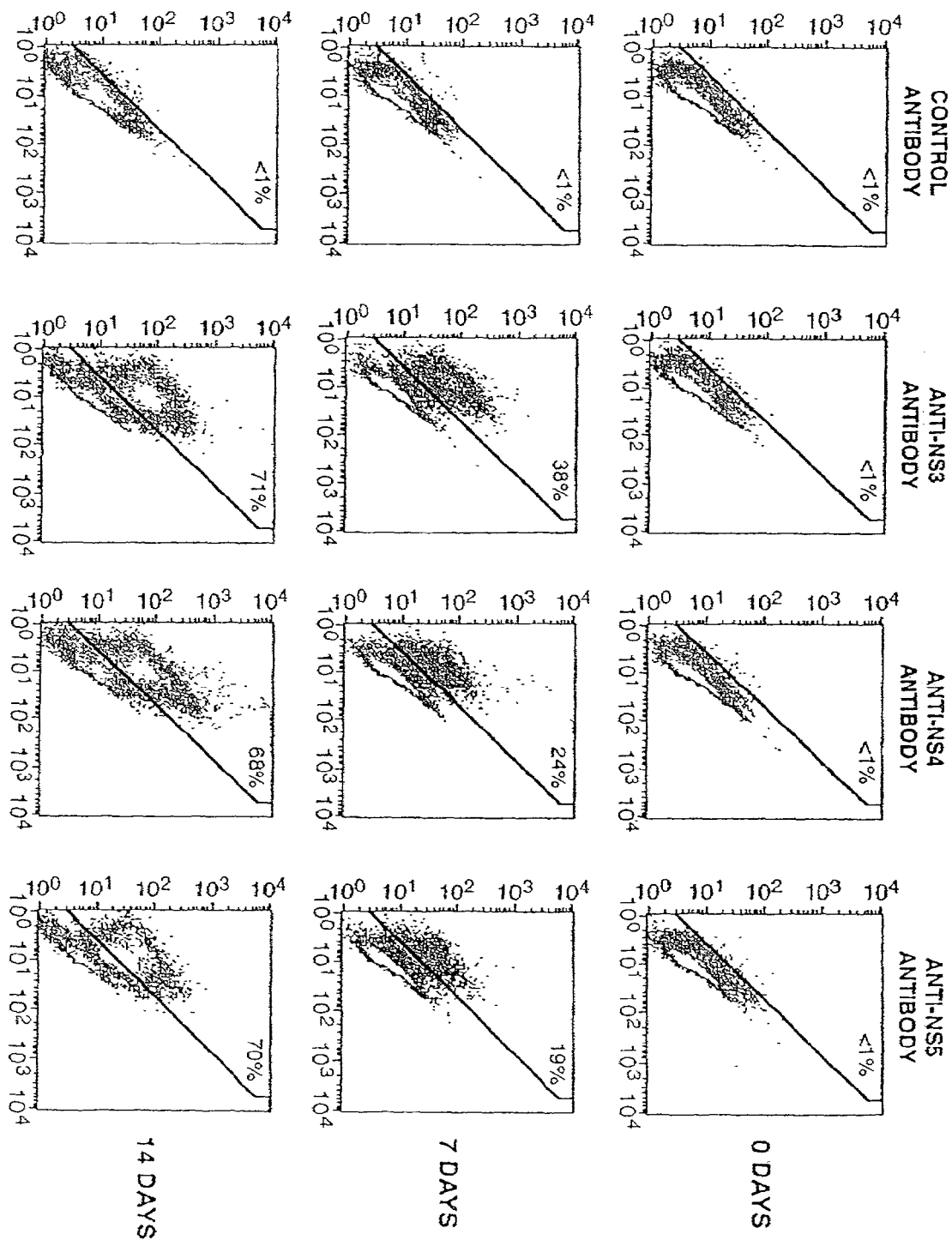
FIG. 2 illustrates intracellular flow cytometric analyses of expression of the HCV nonstructural proteins. the permeabilization and staining of infected Huh-7 cells was performed by using a standard protocol and kit supplied by the manufacturer (BD Pharmingen, San Diego, Calif.). The primary anti-NS3, -NS4, and -NS5 antibodies were purchased from Austral Biologicals. The secondary antibody goat anti-mouse-PE is the same as used for labeling in FIG. 1.
Figure 3:
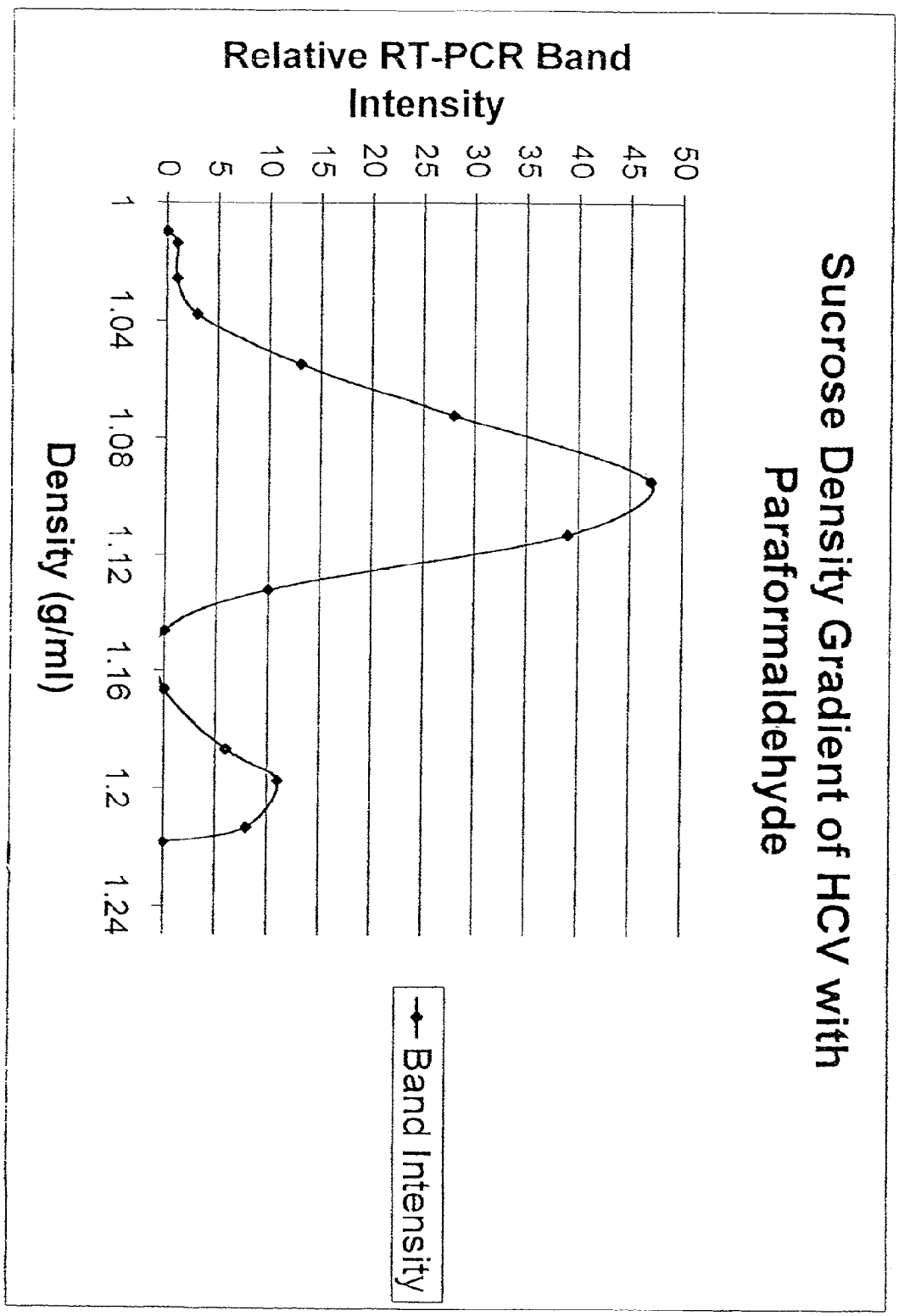
FIG. 3 is a graph showing the Sucrose Density Gradient of HCV with Paraformaldehyde.

In a parallel experiment the same virus preparation was used to infect Huh-7 cells for 7 and 14 days for intracellular staining with antibodies specific for HCV non-structural proteins. Flow cytometric analysis revealed presence of NS3, NS4 and NS5 in almost 70% of the cells in culture implying that close to 70% of the cells were infected with the passaged virus (FIG. 2). These results have been confirmed by successfully generating and passaging infectious HCV from cells transfected with the type 1b HCV plasmid.

Example 8

Visualization of Infectious Virus Particles

To determine whether infectious virus particles could be visualized by electron microscopy, mock- and virus-infected cell monolayers (10 days) were stained with gold particle (10 nm)-conjugated goat anti-mouse antibody that recognizes anti-E1 and anti-E2 antibodies. Cells were grown on 0.45 µm Transwell membranes in 6-well plates (Costar) and infected with serially passaged supernatants derived from an initial control (transfection reagent only) or plasmid DNA (AR3126+pCVH77C) transfected cells as described for FIG. 1. Ten days post-infection, the cells were fixed in PBS containing 3% paraformaldehyde and 1% glutaraldehyde, overnight at 4° C. The fixed cells were then washed with PBS and incubated with 20% normal goat serum (NGS) in PBS for blocking. Cells were then stained with mouse anti-E1/E2 primary antibody (or isotype control) as described for FIG. 1, but in the presence of 2% NGS overnight at 4° C. Cells were washed with PBS and incubated overnight with secondary antibody consisting of 10 nm gold particles linked to goat anti mouse antibody (Ted Pella, Inc., Redding, Calif.), in the presence of 2% NGS. Cells were then postfixed with 1% osmium tetroxide in PBS, dehydrated with ethanol and embedded in Epon. Approximately 70 nm thick sections were prepared and stained with uranyl acetate and lead citrate and examined by transmission electron microscopy under a JEOL-100CX electron microscope (JEOL Ltd., Tokyo, Japan).

Electron micrographs of thin sections of the monolayers showed significant damage of infected cells compared to mock-infected cells including damaged nucleus and other organelles. Clusters of gold particles of approximately 40–60 nm in size were detected in and around membranous structures. No gold particles could be detected in uninfected cells. A more careful analysis of the gold particle clusters at higher magnifications showed images consistent with viral particles at various stages of assembly. Some viral particles detected were in the process of budding from what appeared to be ER or membranous structures reminiscent of ER/Golgi while others appeared to have already been released into the cytoplasm. The viral envelope was clearly visible on some particles. Initial results from density gradient analysis of the passaged virus were found to be consistent with the approximate size of the virus observed by EM.

It is noted that the type 1a H77C plasmid used herein contains two T7 promoters at 5' and 3' termini flanking the HCV sequence. Thus, both positive- and negative-strands of RNA are likely to be produced in cells initially transfected with pCVH77C and AR3126. Only cells transfected with the plasmid containing both the 5' and 3' promoters secrete infectious virus particles; deletion of the 3' T7 promoter from the pCVH77C renders it noninfectious although high quantities of (+) RNA is synthesized in these cells. It is believed that the presence of both (+) and (–) RNA is crucial for production of infectious virus because synthesis of high quantities of one or more viral proteins may be detrimental to virus replication due to toxicity or cellular injury (M. M. C. Lai, C.F. Ware. Curr. Topics in Micro and Immunology. 242:117–134 (2000); D. Moradpour, P. Kary, C. M. Rice, H. E. Blum. Hepatology 28:1920201. (1998).). Consistent with this notion is the recent finding that cells transfected with the pCVH77C, where only (+) strand RNA is synthesized, do not produce infectious virus (D. Moradpour, P. Kary, C. M. Rice, H. E. Blum. Hepatology 28:1920201. (1998).). The minus-strand RNA may attenuate protein synthesis, whereby small amounts of proteins are synthesized over longer periods of time thus facilitating viral replication and release of new viruses into the medium. Alternatively, the dsRNA produced in vitro may evoke the IFN-pathway that may be conducive to slow and sustained growth of HCV.

TABLE 1

| Cell Line | % E1 | % E2 |
|---|---|---|
| HeLa | 3 | 2 |
| Huh-7 | 20 | 22 |

Cell surface expression of HCV E1 and E2 in Huh-7 vs. HeLa cells. Cells were transfected with HCV clone and T7 polymerase for 5 days before FACS analysis. Results show that human liver cells but not HeLa cells support E1 and E2 expression.

TABLE 2

| Untreated Supernatant | | DNase & Rnase Treated Supernatant | |
|---|---|---|---|
| % E1 | % E2 | % E1 | % E2 |
| 25 | 89 | 20 | 82 |

Media recovered from cells transfected with HCV cDNA and T7 RNA polymerase gene were used to infect fresh Huh-7 cells before (untreated) and after treatment with a mixture of DNase and RNase. The results show that the infection of fresh cells with the cell-free media is due to encapsidated virus and not due to contaminating HCV DNA or RNA.

Although the invention has been described with reference to the above examples, it will be understood that modifications and variations are encompassed within the spirit and scope of the invention. Accordingly, the invention is limited only by the following claims.

What is claimed is:

1. A culture system for generating infectious hepatitis C virus (HCV) comprising preparing a cell culture medium from a cell culture, the cell culture produced by transfecting a hepatocyte cell with a nucleic acid sequence encoding HCV and nucleic acid sequence encoding RNA polymerase under conditions suitable for transfecting the cell, wherein following transfection, the cell culture medium contains infectious HCV.

2. The culture system of claim 1, further comprising exposing the cell culture medium to a non-transfected hepatocyte cell, wherein following exposure, infectious HCV is secreted from the non-transfected hepatocyte cell.

3. The culture system of claim 2, wherein the non-transfected hepatocyte cell is co-cultured with the transfected cell.

4. The culture system of claim 1 or 2, further comprising isolating the cell culture medium containing infectious HCV.

5. The culture system of claim 1, wherein the nucleic acid sequence encoding HCV and the nucleic acid sequence encoding RNA polymerase are in a single plasmid.

6. The culture system of claim 1, wherein the nucleic acid sequence encoding HCV is contained in a first plasmid and the nucleic acid sequence encoding RNA polymerase is in a second plasmid.

7. The culture system of claim 1, wherein the transfecting comprises transfecting the hepatocyte cell with a nucleic acid sequence encoding NS3 and NS5B.

8. The culture system of claim 7, wherein the nucleic acid sequence encoding HCV, the nucleic acid sequence encoding RNA polymerase and nucleic acid sequence encoding NS3 and NS5B are in a single plasmid.

9. The culture system of claim 7, wherein nucleic acid sequence encoding HCV, the nucleic acid sequence encoding RNA polymerase and nucleic acid sequence encoding NS3 and NS5B are contained in more than one plasmid.

10. The culture system of claim 1 or 2, wherein the hepatocyte cells are derived from human tissue.

11. The culture system of claim 10, wherein the hepatocyte cells are hepatocellular carcinoma cells.

12. The culture system of claim 11, wherein the cell is Huh-7, HepG2, C3A or PLC.

13. The culture system of claim 1, wherein the HCV is type 1a HCV or type 1b HCV.

14. The culture system of claim 1, wherein the RNA polymerase is a T7 RNA polymerase.

15. The culture system of claim 1, wherein the nucleic acid sequence encoding HCV includes a promoter, wherein the promoter is activated by the RNA polymerase.

16. The culture system of claim 15, wherein the promoter is T7, SP6 or QB.

17. A method for generating infectious hepatitis C virus (HCV) comprising preparing a cell culture medium from a cell culture, the cell culture produced by transfecting a hepatocyte cell with a nucleic acid sequence encoding HCV and nucleic acid sequence encoding RNA polymerase under conditions suitable for transfecting the cell, wherein following transfection, the cell culture medium contains infectious HCV.

18. The method of claim 17, further comprising exposing the cell culture medium to a non-transfected hepatocyte cell, wherein following exposure, infectious HCV is secreted from the non-transfected hepatocyte cell.

19. The method of claim 18, wherein the non-transfected hepatocyte cell is co-cultured with the transfected cell.

20. The method of claim 17 or 18, further comprising isolating the cell culture medium containing infectious HCV.

21. The method of claim 17, wherein the nucleic acid sequence encoding HCV and the nucleic acid sequence encoding RNA polymerase are in a single plasmid.

22. The method of claim 17, wherein the nucleic acid sequence encoding HCV is contained in a first plasmid and the nucleic acid sequence encoding RNA polymerase is in a second plasmid.

23. The method of claim 17, wherein the transfecting comprises transfecting the hepatocyte cell with a nucleic acid sequence encoding NS3 and NS5B.

24. The method of claim 23, wherein the nucleic acid sequence encoding HCV, the nucleic acid sequence encoding RNA polymerase and nucleic acid sequence encoding NS3 and NS5B are in a single plasmid.

25. The method of claim 23, wherein nucleic acid sequence encoding HCV, the nucleic acid sequence encoding RNA polymerase and nucleic acid sequence encoding NS3 and NS5B are contained in more than one plasmid.

26. The method of claim 17 or 18, wherein the hepatocyte cells are derived from human tissue.

27. The method of claim 26, wherein the hepatocyte cells are hepatocellular carcinoma cells.

28. The method of claim 27, wherein the cell is Huh-7, HepG2, C3A or PLC.

29. The method of claim 17, wherein the HCV is type 1a HCV or type 1b HCV.

30. The method of claim 17, wherein the RNA polymerase is a T7 RNA polymerase.

31. The method of claim 17, wherein the nucleic acid sequence encoding HCV includes a promoter, wherein the promoter is activated by the RNA polymerase.

32. The method of claim 31, wherein the promoter is T7, SP6 or QB.

* * * * *

UNITED STATES PATENT AND TRADEMARK OFFICE
CERTIFICATE OF CORRECTION

| | | |
|---|---|---|
| PATENT NO. | : 7,183,095 B2 | |
| APPLICATION NO. | : 10/096039 | |
| DATED | : February 27, 2007 | |
| INVENTOR(S) | : Dasgupta and Koka | |

It is certified that error appears in the above-identified patent and that said Letters Patent is hereby corrected as shown below:

COLUMN 1, LINE 10

Add the following title and paragraph beginning on Line 10 of Column 1 prior to the paragraph entitled "FIELD OF THE INVENTION", specifically:

--GRANT INFORMATION

This invention was made in part with government support under Grant No. AI45733 awarded by the National Institutes of Health. The government has certain rights in this invention.--

Signed and Sealed this

Seventh Day of August, 2007

JON W. DUDAS
*Director of the United States Patent and Trademark Office*